(12) United States Patent
Marini et al.

(10) Patent No.: US 10,179,103 B1
(45) Date of Patent: Jan. 15, 2019

(54) ANTI-CELLULITE CREAM

(71) Applicant: Jan Marini Skin Research, San Jose, CA (US)

(72) Inventors: Jan L. Marini, San Jose, CA (US); Subhash J. Saxena, Ringoes, NJ (US)

(73) Assignee: Jan Marini Skin Research, San Jose, CA (US)

( * ) Notice: Subject to any disclaimer, the term of this patent is extended or adjusted under 35 U.S.C. 154(b) by 0 days.

(21) Appl. No.: 15/981,570

(22) Filed: May 16, 2018

(51) Int. Cl.
| | |
|---|---|
| *A61K 8/9789* | (2017.01) |
| *A61K 8/49* | (2006.01) |
| *A61K 8/41* | (2006.01) |
| *A61K 8/64* | (2006.01) |
| *A61Q 19/06* | (2006.01) |
| *A61K 8/34* | (2006.01) |
| *A61K 8/42* | (2006.01) |
| *A61K 8/02* | (2006.01) |
| *A61K 8/73* | (2006.01) |

(52) U.S. Cl.
CPC .......... *A61K 8/9789* (2017.08); *A61K 8/0216* (2013.01); *A61K 8/342* (2013.01); *A61K 8/416* (2013.01); *A61K 8/42* (2013.01); *A61K 8/4926* (2013.01); *A61K 8/4953* (2013.01); *A61K 8/64* (2013.01); *A61K 8/733* (2013.01); *A61Q 19/06* (2013.01)

(58) Field of Classification Search
None
See application file for complete search history.

(56) References Cited

U.S. PATENT DOCUMENTS

| | | |
|---|---|---|
| 6,328,987 B1 | 12/2001 | Marini |
| 6,821,524 B2 | 11/2004 | Marini |
| 8,318,678 B2 | 11/2012 | Marini |
| 9,089,505 B1 | 7/2015 | Saxena et al. |
| 9,572,767 B2 | 2/2017 | Marini et al. |
| 9,693,947 B1 | 7/2017 | Marini et al. |
| 9,808,654 B2 | 11/2017 | Marini et al. |
| 2007/0196318 A1 | 8/2007 | Marini |
| 2009/0263513 A1 | 10/2009 | Marini |
| 2010/0247693 A1 | 9/2010 | Marini |
| 2013/0189211 A1 | 7/2013 | Marini |
| 2017/0000716 A1 | 1/2017 | Marini et al. |
| 2017/0056309 A1 | 3/2017 | Marini et al. |
| 2017/0258697 A1 | 9/2017 | Marini et al. |

FOREIGN PATENT DOCUMENTS

| | | |
|---|---|---|
| EP | 1203579 A1 | 5/2002 |
| EP | 1369107 A1 | 12/2003 |
| EP | 1825845 A1 | 8/2007 |
| WO | 2009/148551 A1 | 12/2009 |

*Primary Examiner* — Susan Hoffman
(74) *Attorney, Agent, or Firm* — Pamela J. Sherwood; Bozicevic, Field & Francis LLP

(57) ABSTRACT

The present invention features novel cosmetic skin care compositions for improving the appearance of skin, and particularly for improving the appearance of cellulite.

7 Claims, 2 Drawing Sheets
(2 of 2 Drawing Sheet(s) Filed in Color)

ANTI-CELLULITE CREAM

INTRODUCTION

Cellulite (also known as adiposis edematosa, dermopanniculosis deformans, status protrusus cutis, gynoid lipodystrophy, liposclerosis, edematofibrosis and orange peel syndrome) is a skin care concern believed to result from herniation of subcutaneous fat within fibrous connective tissue. It manifests topographically as skin dimpling and nodularity, often on the pelvic region (hips and buttocks), upper and lower limbs, and abdomen. Hormonal factors appear to play a role in the formation of cellulite; it occurs in approximately 80-90% of post-adolescent females, and it is less often seen in males with the exception of those with androgen-deficient states, such as Klinefelter's syndrome, hypogonadism, or postcastration, and in patients receiving estrogen therapy for prostate cancer.

Hormones such as estrogen, insulin, the catecholamines adrenaline and noradrenaline, thyroid hormones and prolactin are believed to play a role in the development of cellulite. In addition to hormones, a complex combination of factors contributing to the formation of cellulite including sex and sex-specific dimorphic skin architecture, alteration of connective tissue structure, genetic factors and heredity, race, biotype, changes in metabolism, physiology, diet and exercise habits, obesity, distribution of subcutaneous fat, the extracellular matrix, the microcirculatory system, predisposition to lymphatic and circulatory insufficiency and subtle inflammatory alterations. Furthermore, a high-stress lifestyle can cause an increase in the level of catecholamines, which have been associated with the development of cellulite.

With regard to a hereditary contribution to an individual's susceptibility to development of cellulite, researchers led by Enzo Emanuele have traced a genetic component of cellulite formation to particular polymorphisms in the angiotensin converting enzyme (ACE) and hypoxia-inducible factor 1A (H1F1a) genes.

The appearance of cellulite can be categorized into four grades, using the Nürnberger-Müller cellulite classification scale (Michael H. Gold, 2012 *J. German Soc. Dermat.* 10:553-558). Stage 0=No dimpling when the subject is standing and lying. The pinch test reveals "folds and furrows", but there is no mattress-like appearance.
Stage 1=No dimpling when the subject is standing or lying, but the pinch test reveals the mattress-like appearance.
Stage 2=Dimpling appears spontaneously when standing and not lying down.
Stage 3=Dimpling is spontaneously positive standing and lying down.

Cosmetic compositions that improve skin tone, texture, luminosity, resilience, and the appearance of cellulite, remain of great interest to consumers and nearly all major cosmetic and skin care companies.

SUMMARY

The present disclosure provides cosmetic formulations and methods for improving the appearance of the skin, and specifically for improving the appearance of skin dimpling, nodularity and cellulite. The compositions disclosed herein are designed for use as a lotion, cream or gel, for use in improving the appearance of skin dimpling, nodularity and cellulite in a subject.

According to a first aspect of the present disclosure, provided herein is a cosmetic composition for topical application, comprising a specific and efficacious blend of fat dehydrating, fat dissolving and/or fat metabolizing agents, and skin firming agents, including caffeine, L-carnitine, aminophylline, methylsilanol carboxymethyl theophylline alginate, tripeptide-41, acetyl decapeptide-3, glaucine, capsaicin, *Nelumbo nucifera* (lotus) flower extract, *Brassica alba* (mustard) sprout extract and retinol.

According to a second aspect of the present disclosure, a method is provided for improving the appearance of the skin, in particular to improve the appearance of skin dimpling, nodularity and cellulite, the method comprising applying topically a cosmetic cream, lotion or gel composition comprising an efficacious blend of caffeine, L-carnitine, aminophylline, methylsilanol carboxymethyl theophylline alginate, tripeptide-41, acetyl decapeptide-3, glaucine, capsaicin, *Nelumbo nucifera* (lotus) flower extract, *Brassica alba* (mustard) sprout extract and retinol.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1B show the results of use of CelluliTx cream. The cream was applied twice daily for one month (FIG. 1A) and for 2 months (FIG. 1B). The results show a dramatic change in skin tone after regular use of the product.

DETAILED DESCRIPTION OF THE EMBODIMENTS

Disclosed herein are topical compositions and methods that employ a plurality of pathways leading to reduction of undesirable dimpling and improvement in the appearance of cellulite, producing visible results as early as about 2 weeks, about 4 weeks, about 6 weeks, about 8 weeks, about 12 weeks.

The present disclosure provides topical compositions designed for use as a lotion, cream or gel, for use in improving the appearance of the skin, particularly undesirable skin dimpling, nodularity and cellulite. The herein disclosed cosmetic compositions for topical application include a cosmetically acceptable vehicle to act as a diluent, dispersant or carrier for the active agents, so as to facilitate distribution and uptake when the composition is applied as a skin cream, which may be applied daily, twice daily, e.g. morning and night. Vehicles other than water can include liquid or solid emollients, solvents, humectants, thickeners and powders. The cosmetically acceptable vehicle will usually form 5% to 99.9%, or from about 25% to 80%, or from about 40% to 60%, by weight of the composition, and can, in the absence of other cosmetic adjuncts, form the balance of the composition. The compositions presently disclosed comprise a specific and efficacious blend of fat dehydrating, fat dissolving and/or fat metabolizing agents, and skin firming agents, including caffeine, L-carnitine, aminophylline, methylsilanol carboxymethyl theophylline alginate, tripeptide-41, acetyl decapeptide-3, glaucine, capsaicin,

*Nelumbo nucifera* (lotus) flower extract, *Brassica alba* (mustard) sprout extract and retinol.

As noted, the compositions may be in the form of an aqueous cream, lotion or gel. The presently disclosed compositions may be formulated according to the usual techniques as are well known to this art. The compositions of the invention may further comprise cosmetically useful agents and excipients, e.g. glycerin, cetyl alcohol, capric triglyceride, glyceryl stearate, PEG-100 stearate, steareth-20, steareth-2, cyclopentasiloxane, phenoxyethanol, lecithin, tocopherol, aloe vera, etc. each at a concentration of from about 0.1% to about 10% by weight, usually from about 0.5% to about 5%, and may be present at a concentration of from about 0.5%, 1%, 2%, 3%, 4%, 5%, etc. by weight.

The compositions of the present invention provide a range of factors that stimulate fat cells to metabolize instead of store fat. In the cosmetic industry, a long-felt need remains for compositions that activate microcirculation in the skin fat tissue and that improve the appearance of fat and overlying skin. In addition to white adipose tissue (WAT) known to store fat, humans possess a pool of brown adipose tissue (BAT). WAT and BAT differ in composition, function and lipid and mitochondria content. Mitochondria are especially numerous in brown adipocytes, and mitochondria are responsible for generation of ATP via the electron transport chain. In brown adipocytes, the proton gradient is short circuited by high expression of the protein UCP1. UCP1 is reported to form another channel through which protons leak from adipocytes, uncoupling protons from the electron transport chain and ATP generation; therefore, BAT can generate heat. The use of glucose and fatty acids to fuel this process leads to an increase in basal energy expenditure and can be used to promote weight loss. (Wandrey, et al., Sep. 9, 2016, *SOFW Journal*, vol 142:13-17).

The term "adipocyte browning" is sometimes used to refer to the process of stimulating the production of UCP1, leading to the conversion of normal white fat cells into brown-like adipocytes. Thus, adipocyte browning is considered a promising technology for eliminating fat deposits, such as in cellulite. The best known triggers for the induction of adipocyte browning are cold exposure and activation of the beta3-adrenergic receptor present in fat cells. It has been reported that, in mice, the beta3-adrenergic receptor can be activated by an ethanolic extract of *Brassica campestris* roots, a plant from the mustard family (Brassicaceae); this had an anti-obesity effect on these mice even when they were fed with a high fat diet. Therefore, plants from the mustard family are intriguing candidates to stimulate adipocyte browning. (Wandrey, et al., Sep. 9, 2016, *SOFW Journal*, vol 142:13-17).

Without being bound by theory, one mechanism triggered by the compositions and methods of the present disclosure is browning and stimulation of adipocytes to burn fat through thermogenesis rather than storing fat.

Components of the Cosmetic Compositions

The presently disclosed compositions comprise a specific blend of therapeutic agents, including specifically a combination of caffeine, L-carnitine, aminophylline, methylsilanol carboxymethyl theophylline alginate, tripeptide-41, acetyl decapeptide-3, glaucine, capsaicin, *Nelumbo nucifera* (lotus) flower extract, *Brassica alba* (mustard) sprout extract and retinol; formulated for topical delivery.

Peptides are included that may increase lipolysis and inhibit lipid synthesis. Peptides may also assist in actively generating new skin cells by enhancing fibroblast and keratinocyte cell proliferation to strengthen skin elasticity.

Peptides of particular interest are acetyl decapeptide-3 (such as in the commercially available formulation Rejuline™) and Tripeptide-41 (such as in the commercially available formulation CG-Lipoxyn™) (both available from CAREGEN CO., LTD, Korea). The peptide agents included in the present compositions and methods are formulated at an effective concentration, i.e., at a concentration that provides the intended benefit when applied topically. In some embodiments, an effective concentration of peptide or peptide-like compound may be in a range of at least about 0.0001% to about 1%; for example, at least about 0.001% to about 0.01% of the finished formula composition.

Tripeptide-41 increases lipolysis and inhibits lipid synthesis. In some embodiments, tripeptide-41 is in the form of the commercially available formulation CG-Lipoxyn™ (CAREGEN CO., LTD, Korea). In some embodiments, an effective concentration of tripeptide-41 by weight in the composition may be in a range of at least about 0.0001% to about 0.01%; for example, from about 0.001% to about 0.01%; from about 0.001% to about 0.005%; and may be from about 0.002% to about 0.005% of the finished formula composition, or around about 0.003%.

In some embodiments, the peptide is provided as a component of CG-Lipoxyn™ which may be present by weight in the composition in a range of at least about 0.1% to about 10%; for example, at least about 0.5% to about 5%; at least about 1% to about 3%; at least about 0.1% to about 3.0%; at least about 0.1% to about 1%; at least about 0.5% to about 1.5%; or at least about 1.5 to 4.5% by weight of the finished formula composition.

Acetyl Decapeptide-3 (commercially available as the formulation Rejuline™ from CAREGEN CO., LTD, Korea) is a ten amino acid water soluble peptide having anti-aging and skin-firming qualities. Acetyl Decapeptide-3 actively generates new skin cells (enhances fibroblast and keratinocyte cell proliferation), strengthens skin elasticity by inducing the synthesis of collagen and elastin, and firms skin by increasing the level of extracellular matrix. In some embodiments, acetyl decapeptide-3 may be provided in the form of a commercially available solution called Rejuline™ (CAREGEN CO., LTD, Korea). In some embodiments, an effective concentration of acetyl decapeptide-3 by weight in the composition may be in a range of by weight in the composition from about 0.0001% to about 0.01%; for example, from about 0.001% to about 0.01%; from about 0.001% to about 0.005%; and may be from about 0.0008% to about 0.002% of the finished formula composition, or around about 0.001%. of the finished formula composition.

In some embodiments, the peptide is provided as a component of Rejuline™ which may be present by weight in the composition in a range of at least about 0.1% to about 10%; for example, at least about 0.1% to about 3.0%; at least about 0.5% to about 5%; at least about 0.5 to 3.5%; at least about 0.5% to about 1.5%; at least about 1% to about 3%; at least about 0.1% to about 1%; or at least about 1.5 to 4.5% by weight of the finished formula composition.

Caffeine is effective in reducing local fat, as it helps expel the fat from fat cells in the specific area where it is applied. Caffeine works like a diuretic, and can dehydrate the water content of fat cells, such that fat cells are less swollen, and cellulite shrinks or appears less obvious. Caffeine also helps blood flow to the skin. In some embodiments, an effective concentration of caffeine by weight in the composition is from 0.5 to 3.5%. In some embodiments, an effective concentration of caffeine (in some embodiments in the form of caffeine anhydrous F.C.C.) may be in a range of at least about 0.0001% to about 10%; for example, at least about 0.001% to about 0.01%; at least about 0.01% to about 0.1%; at least about 0.1% to about 1.0%; at least about 1% to about 5%; at least about 0.1% to about 5%; or at least about 1% to about 3% of the finished formula composition, and may be present at around 2% by weight.

L-Carnitine is a naturally occurring amino acid which the body produces, and acts as a functional active ingredient in the presently disclosed composition. L-Carnitine assists the body in metabolizing fat, thereby acting as an anti-cellulite agent. Specifically, L-carnitine can make it easier for the body to oxidize fat, especially stored fat, and transform it into energy. In some embodiments, an effective concentration of L-carnitine (or L-carnitine hydrochloride) by weight in the composition is from 0.5 to 2.5%. In some embodiments, an effective concentration of L-carnitine may be in a range of from about 0.0001% to about 10%; for example, from about 0.001% to about 0.01%; from about 0.01% to about 0.1%; from about 0.1% to about 1.0%; from about 1% to about 5%; from about 0.1% to about 5%; or from about 0.2% to about 3% of the finished formula composition and may be present at around 1%.

Aminophylline, when applied topically, simply dissolves fatty deposits underneath the skin. Aminophylline (in some embodiments, Aminophylline anhydrous USP) dehydrates the skin in and around the area where it is applied. The body then absorbs extra water in the skin. Consequently, the dried skin is pulled taut over fat deposits, which masks the presence of cellulite. In some embodiments, an effective concentration of aminophylline by weight in the composition is from 0.5 to 2.5%. In some embodiments, an effective concentration of aminophylline may be in a range of from about 0.0001% to about 10%; for example, from about 0.001% to about 0.01%; from about 0.01% to about 0.1%; from about 0.1% to about 1.0%; from about 1% to about 5%; from about 0.1% to about 3%; or from about 0.5% to about 1.5% of the finished formula composition and may be present at around 1%.

Methylsilanol carboxymethyl theophylline alginate activates lipolysis which opposes the storage of unsaturated fatty acid. Theophylline alginate is a natural extract of green tea which helps stimulate the fat cells to release the build-up of unwanted toxins. In some embodiments, an effective concentration of methylsilanol carboxymethyl theophylline alginate by weight in the composition is from 0.005 to 0.5% by weight. In some embodiments, methylsilanol carboxymethyl theophylline alginate is provided via the commercially available composition Theophyllisilane 4 (containing methylsilanol carboxymethyl theophylline alginate). In some embodiments, an effective concentration of methylsilanol carboxymethyl theophylline alginate may be in a range of at least about 0.0001% to about 0.1%; for example, from about 0.005% to about 0.05%; from about 0.008% to about 0.02%; from about 0.01% to 0.02% and may be present at about 0.015% of the finished formula composition.

Glaucine is a derivative of the yellow poppy plant. Glaucine is a potent ingredient in the presently described compositions for the reduction of skin dimpling or improving the appearance of cellulite. Glaucine works by various mechanisms, e.g. by encouraging lipolysis, discouraging growth of new fat cells from fibroblasts, reducing water content and increasing firmness of skin. Glaucine is also an anti-inflammatory agent. In some embodiments, an effective concentration of glaucine by weight in the composition may be in a range of from about 0.0001% to about 0.01%; for example, from about 0.0008% to about 0.002%; and may be present at about 0.001% of the finished formula composition.

*Nelumbo nucifera* is also known as Indian lotus, sacred lotus, bean of India, Egyptian bean or simply lotus, is one of two extant species of aquatic plant in the family Nelumbonaceae. *Nelumbo nucifera* is an aquatic perennial, and under favorable circumstances its seeds may remain viable for many years, with the oldest recorded lotus germination being from that of seeds 1,300 years old recovered from a dry lakebed in northeastern China. *Nelumbo nucifera* flower extract (commercially available, for example, in the composition PRO-SVELTYL®) is rich in flavonoids. In the presently described compositions, *Nelumbo nucifera* (lotus) flower extract reduces fat storage, prevents tissue inflammation and preserves the fiber architecture of the skin. It acts as a strong anti-cellulite agent, improving the functionality of adipose tissue. In some embodiments, an effective concentration of *Nelumbo nucifera* (lotus) flower extract by weight in the composition may be in a range of from about 0.0001% to about 0.01%; for example, from about 0.001% to about 0.05%; 0.001% to about 0.01%, from about 0.005% to about 0.009%, and may be present at about 0.0085% of the finished formula composition.

Capsaicin is an active component of chili peppers. Capsaicin has a warming and anti-inflammatory effect on the skin. Capsaicin also works to increase blood flow. In some embodiments, an effective concentration of capsaicin by weight in the composition may be in a range of at least about 0.0001% to about 0.1%; for example, from about 0.0001% to about 0.01%; from about 0.002% to about 0.008%; and may be around about 0.005% of the finished formula composition.

*Brassica alba* (Mustard) sprout extract is a lipid soluble anti-cellulite slimming ingredient. It is a vasodilator that activates microcirculation and therefore fights water retention in cellulite tissue. Additionally, it "empties" the cells of the adipose tissue by converting fat-accumulating adipocytes into cells that actively burn fat. In some embodiments, an effective concentration of capsaicin by weight in the composition may be in a range of from about 0.0001% to about 0.1%; for example, from about 0.001% to about 0.01%; from about 0.002% to about 0.008%; and may be around about 0.005% of the finished formula composition.

ShapePerfection is a commercially available composition containing caprylic/capric triglyceride, capsaicin and *Brassica alba* (mustard) sprout extract. In some embodiments, an effective concentration of ShapePerfection by weight in the composition may be in a range of from about 0.001% to about 0.05%; from about 0.005% to about 0.05%; from about 0.01% to about 0.1%; from about 0.1% to about 1.0%; or from about 0.5% to about 2.5% of the finished formula composition.

Retinol (CAS number 68-26-8; also known as "(2E,4E,6E,8E)-3,7-dimethyl-9-(2,6,6-trimethylcyclohex-1-enyl)nona-2,4,6,8-tetraen-1-ol") works by being able to penetrate the skin, exfoliate it, and increase collagen production, which makes skin thicker and hides the dimpling fat. In some embodiments, an effective concentration of retinol may be present at a concentration of from 0.1 to 0.6% by weight in the composition. For example, retinol may be in a range of at least about 0.001% to about 2%; for example, from about 0.1% to about 0.6%, from about 0.1% to about 0.3%, and may be present at around about 0.2% of the finished formulation.

In some embodiments, retinol may be in the form of a composition RETINOL 50C, and retinol by comprise 0.40% by weight in the final composition. Formulations with higher or lower concentrations of retinol are available, where a high dose may have from about 0.5% to about 1% retinol, for example at about 0.75%. A low dose formulation may have from about 0.1% to about 0.49% retinol, for example at around about 0.35%. In some embodiments, an effective concentration of retinol by weight in the composition may be in a range of at least about 0.0001% to about 10%; for example, at least about 0.0001% to about 0.001%; at least about 0.001% to about 0.05%; at least about 0.01% to about 0.1%; at least about 0.1% to about 1.0%; at least about 0.4% to about 1.5%; or at least about 0.5% to about 2.5% of the finished formula composition.

Skin conditioning agents in the formulation can be provided in addition to the active agents described above and may include, but are not limited to, biotin, butylene glycol, isopropyl palmitate, glycerin, glycine Soja (soybean) oil, *Butyrospermum parkii* (Shea) Butter, caprylic/capric triglyceride, cyclopentasiloxane, lecithin, C13-14 isoparaffin, sclerotium gum, xanthan gum, bisabolol, tocopheryl acetate, sodium PCA and capsaicin.

The compositions of the invention may optionally comprise other skin benefit materials. These include estradiol; progesterone; pregnanalone; coenzyme Q10; methylsolanomethane (MSM); copper peptide (copper extract); plankton extract (phytosome); kojic acid; broparoestrol; estrone; adrostenedione; androstanediols; hydroquinone; isoflavones, etc. The steroids will generally be present at a concentration of less than about 5% or about 10% of the total by weight of the composition, while the other skin benefit materials may be present at higher levels, for example as much as about 10 to about 15%.

The amounts of cosmetic or dermatological auxiliaries and additives and perfume to be used in each case can easily be determined by simple exploratory experiments by the person skilled in the art, depending on the nature of the product in question. In some embodiments, the compositions described herein are fragrance free and paraben-free.

Cosmetically Acceptable Vehicle

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The compositions of the invention include a cosmetically acceptable vehicle to act as a diluent, dispersant or carrier for the active agents, so as to facilitate distribution and uptake when the composition is applied as a cream. Vehicles other than or in addition to water, triglycerides, glycerol, etc. can include liquid or solid emollients, solvents, humectants, thickeners and powders. The cosmetically acceptable vehicle will usually form 5% to 99.9%, preferably from 25% to 80%, about 40% to 60%, by weight of the composition, and can, in the absence of other cosmetic adjuncts, form the balance of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present disclosure are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, the presently disclosed cosmetic compositions in the form of a cream, lotion or gel, and methods for topical application for reducing skin dimpling and improving the appearance of cellulite. The cream, lotion or gel includes anti-cellulite agents, such as, for example, from 0.5 to 3.5% by weight caffeine; from 0.5 to 2.5% by weight L-carnitine; from 0.5 to 2.5% by weight aminophylline; from 1.5 to 4.5% by weight Lipoxyn (Tripeptide-41); from 0.5 to 3.5% by weight Rejuline (acetyl decapeptide-3); from 0.5 to 2.5% by weight Theophyllisilane 4 (containing methylsilanol carboxymethyl theophylline alginate), from 0.5 to 2.5% by weight *Nelumbo nucifera* (lotus) flower extract; from 0.1 to 0.6% by weight retinol; and from 0.5 to 2.5% by weight ShapePerfection (containing capsaicin and *Brassica alba* (mustard) sprout extract) or alternatively may comprise capsaicin and *Brassica alba* sprout extract as individually formulated components; and a cosmetically acceptable vehicle in an emulsion suitable for administration as a cream, lotion or gel. Furthermore, a composition of the invention may include additional agents or additives that are not in themselves active agents but play a role in promoting the usefulness or effectiveness of an active agent.

Compositions of the present disclosure may be applied to any subject and used to treat a variety of conditions, particularly for the reducing the appearance of skin dimpling and improving the appearance of cellulite. A typical composition of the present disclosure is formulated as a cream, which may be applied topically once or twice daily.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area, e.g. the thighs, buttocks, abdomen, breasts, arms, etc.

The cosmetic composition of the present disclosure can be formulated in any form suitable for application to the site of interest, including a lotion, cream, gel, or the like. The composition can be packaged in any suitable container to suit its viscosity and intended use by the consumer. For example, a lotion or cream can be packaged in a bottle, or a propellant-driven aerosol device or a container fitted with a pump suitable for finger and/or manual operation. When the composition is a cream, it can simply be stored in a non-deformable bottle or squeeze container, such as a lidded jar, a pump dispenser, or a tube. The present disclosure accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

Example 1

Example 1 illustrates a topical composition according to the present invention. The composition can be processed in conventional manner and is suitable for cosmetic use. In particular the compositions are suitable for application to a site of interest for the treatment of a variety of skin conditions.

| Marini CelluliTx Cream | | |
| --- | --- | --- |
| CAS number | Name | Final concentration |
| 58-08-2 | caffeine anhydrous | 0.5-3.5% |
| 6645-46-1 | L-carnitine hydrochloride | 0.5-2.5% |
| 317-34-0 | anhydrous aminophylline | 0.5-2.5% |
| | Tripeptide-41 | 0.001-0.005% |
| | acetyl decapeptide-3 | 0.0005-0.005% |
| 128973-73-9 | methylsilanol carboxymethyl theophylline alginate | 0.005-0.05% |
| 8505-51-4 | *Nelumbo Nucifera* (Sacred Lotus) flower extract | 0.001-0.01% |
| 475-81-0 | Glaucine | 0.0005-0.005% |
| 84929-33-9 | *Brassica Alba* (mustard) sprout extract | 0.001-0.01% |
| 404-86-4 | capsaicin | 0.001-0.01% |
| 989-51-5 | retinol | 0.1-0.6% |

Additional ingredients can be included to provide a cosmetically acceptable vehicle and to bring the volume to 100%, comprising one or more of water, C13-14 Isoparaffin, Alcohol, BHA, BHT, Biotin, Bisabolol, Botanistat PF-64, Butylene Glycol, *Butyrospermum Parkii* (Shea) Butter, Caprylic/Capric Triglyceride, Caprylyl Glycol, Citric Acid, Coco-Glucoside, Cyclopentasiloxane, Disodium EDTA, Ethylhexylglycerin, Glyceryl Stearate, Glycerin, Glycine Soja (Soybean) Oil, Hexylene Glycol, Hydrogenated Lecithin, Isopropyl Palmitate, Laureth-7, Lecithin, Palmitic Acid, PEG-100 stearate, Phenoxyethanol, Polyacrylamide, Polysorbate 20, Sclerotium gum, Sodium Acrylates Copolymer, Sodium Benzoate, Sodium Citrate, Sodium Oleate, Sodium PCA, Sorbitan Stearate, Stearyl Alcohol, Tocopheryl Acetate, Xanthan Gum.

As shown in FIG. 1, twice daily use of the topical composition over a period of from 1 to 2 months provides for improved appearance of the skin, and in particular, cellulite.

All publications and patent applications cited in this specification are herein incorporated by reference as if each individual publication or patent application were specifically and individually indicated to be incorporated by reference.

Although the preceding disclosure has been described in detail, it is merely illustrative. It will be readily apparent to those of ordinary skill in the art in light of these teachings that certain changes and modifications may be made thereto without departing from the spirit or scope of the appended claims. Skilled artisans will be able to devise various alternative arrangements which, although not explicitly described or shown herein, embody the principles of the present disclosure, and these also are included within the spirit and scope of the present disclosure. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A cosmetic composition for topical application comprising:

from 0.5 to 3.5% by weight caffeine; from 0.5 to 2.5% by weight L-carnitine hydrochloride; from 0.5 to 2.5% by weight aminophylline; from 0.001 to 0.005% by weight Tripeptide-41; from 0.0005 to 0.005% by weight acetyl decapeptide-3; from 0.005 to 0.05% by weight methylsilanol carboxymethyl theophylline alginate, from 0.001 to 0.01% by weight *Nelumbo nucifera* (lotus) flower extract; from 0.0005 to 0.005% by weight glaucine; from 0.1 to 0.6% by weight retinol; from 0.001 to 0.01% by weight *Brassica alba* sprout extract; from 0.001 to 0.01% capsaicin; and a cosmetically acceptable vehicle.

2. The composition of claim 1, comprising from 1 to 3% by weight caffeine; from 0.5 to 2% by weight L-carnitine hydrochloride; from 0.5 to 2% by weight aminophylline; from 0.002 to 0.005% by weight Tripeptide-41; from 0.0008 to 0.002% by weight acetyl decapeptide-3; from 0.01 to 0.02% by weight methylsilanol carboxymethyl theophylline alginate, from 0.005 to 0.009% by weight *Nelumbo nucifera* (lotus) flower extract; from 0.0008 to 0.002% by weight glaucine; from 0.1 to 0.6% by weight retinol; from 0.002 to 0.008% by weight *Brassica alba* sprout extract; from 0.002 to 0.008% capsaicin; and a cosmetically acceptable vehicle.

3. The composition of claim 1, formulated as a cream.

4. The composition of claim 1, formulated as a lotion.

5. The composition of claim 1, formulated as a gel.

6. A method of improving the appearance of the skin and reducing cellulite, comprising topically applying a cosmetic formulation comprising:

from 0.5 to 3.5% by weight caffeine; from 0.5 to 2.5% by weight L-carnitine hydrochloride; from 0.5 to 2.5% by weight aminophylline; from 0.001 to 0.005% by weight Tripeptide-41; from 0.0005 to 0.005% by weight acetyl decapeptide-3; from 0.005 to 0.05% by weight methylsilanol carboxymethyl theophylline alginate, from 0.001 to 0.01% by weight *Nelumbo nucifera* (lotus) flower extract; from 0.0005 to 0.005% by weight glaucine; from 0.1 to 0.6% by weight retinol; from 0.001 to 0.01% by weight *Brassica alba* sprout extract; from 0.001 to 0.01% capsaicin; and a cosmetically acceptable vehicle.

7. The method of claim 6, wherein the cosmetic formulation comprises from 1 to 3% by weight caffeine; from 0.5 to 2% by weight L-carnitine hydrochloride; from 0.5 to 2% by weight aminophylline; from 0.002 to 0.005% by weight Tripeptide-41; from 0.0008 to 0.002% by weight acetyl decapeptide-3; from 0.01 to 0.02% by weight methylsilanol carboxymethyl theophylline alginate, from 0.005 to 0.009% by weight *Nelumbo nucifera* (lotus) flower extract; from 0.0008 to 0.002% by weight glaucine; from 0.1 to 0.6% by weight retinol; from 0.002 to 0.008% by weight *Brassica alba* sprout extract; from 0.002 to 0.008% capsaicin; and a cosmetically acceptable vehicle.

* * * * *